United States Patent [19]
Leisse et al.

[11] Patent Number: 5,723,026
[45] Date of Patent: Mar. 3, 1998

[54] PROCESS FOR RECOVERING PURE BENZENE AND PURE TOLUENE FROM AROMATIC HYDROCARBON PRODUCTS

[75] Inventors: Martin Leisse; Hans-Jürgen Vollmer; Uwe Ranke, all of Essen, Germany

[73] Assignee: Krupp Koppers GmbH, Essen, Germany

[21] Appl. No.: 517,009

[22] Filed: Aug. 18, 1995

[30] Foreign Application Priority Data

Oct. 21, 1994 [DE] Germany .................. 44 37 702.9

[51] Int. Cl.⁶ .................. B01D 3/40; C07C 7/08
[52] U.S. Cl. .................. 203/58; 202/154; 202/155; 202/172; 203/75; 203/78; 203/82; 203/84; 203/99; 203/DIG. 19; 585/807; 585/865; 585/808
[58] Field of Search .................. 203/58, 39, 73, 203/74, 82, 75, 77, 78, 84, 99, DIG. 19; 585/808, 834, 863, 865, 807; 208/325; 202/154, 155, 172

[56] References Cited

U.S. PATENT DOCUMENTS

| | | |
|---|---|---|
| 3,816,302 | 6/1974 | Paret .................. 208/323 |
| 3,884,769 | 5/1975 | Mikitenko et al. .................. 203/53 |
| 4,162,198 | 7/1979 | Stockburger et al. .................. 203/88 |
| 4,306,945 | 12/1981 | Montanari et al. .................. 203/84 |
| 4,586,986 | 5/1986 | Preusser et al. .................. 203/74 |
| 5,107,055 | 4/1992 | Klaumünzer et al. .................. 585/808 |
| 5,399,244 | 3/1995 | Gentry et al. .................. 203/58 |
| 5,401,365 | 3/1995 | Chen et al. .................. 203/89 |

FOREIGN PATENT DOCUMENTS

| | | |
|---|---|---|
| 0 434 959 | 7/1991 | European Pat. Off. . |
| 1 543 119 | 9/1969 | Germany . |
| 1 568 940 | 12/1978 | Germany . |

*Primary Examiner*—Virginia Manoharan
*Attorney, Agent, or Firm*—Herbert Dubno; Jonathan Myers

[57] ABSTRACT

The production of high purity benzene and high purity toluene is obtained by utilizing the initial gas separating column for the treatment of the aromatic containing starting material as a separating column for separating a benzene rich from a toluene rich component. The benzene rich component is subject directly to distillation while the toluene is subject to predistillation to separate high boiling components and only then to extractive distillation is distilled to separate the high purity benzene from the high purity toluene.

16 Claims, 1 Drawing Sheet

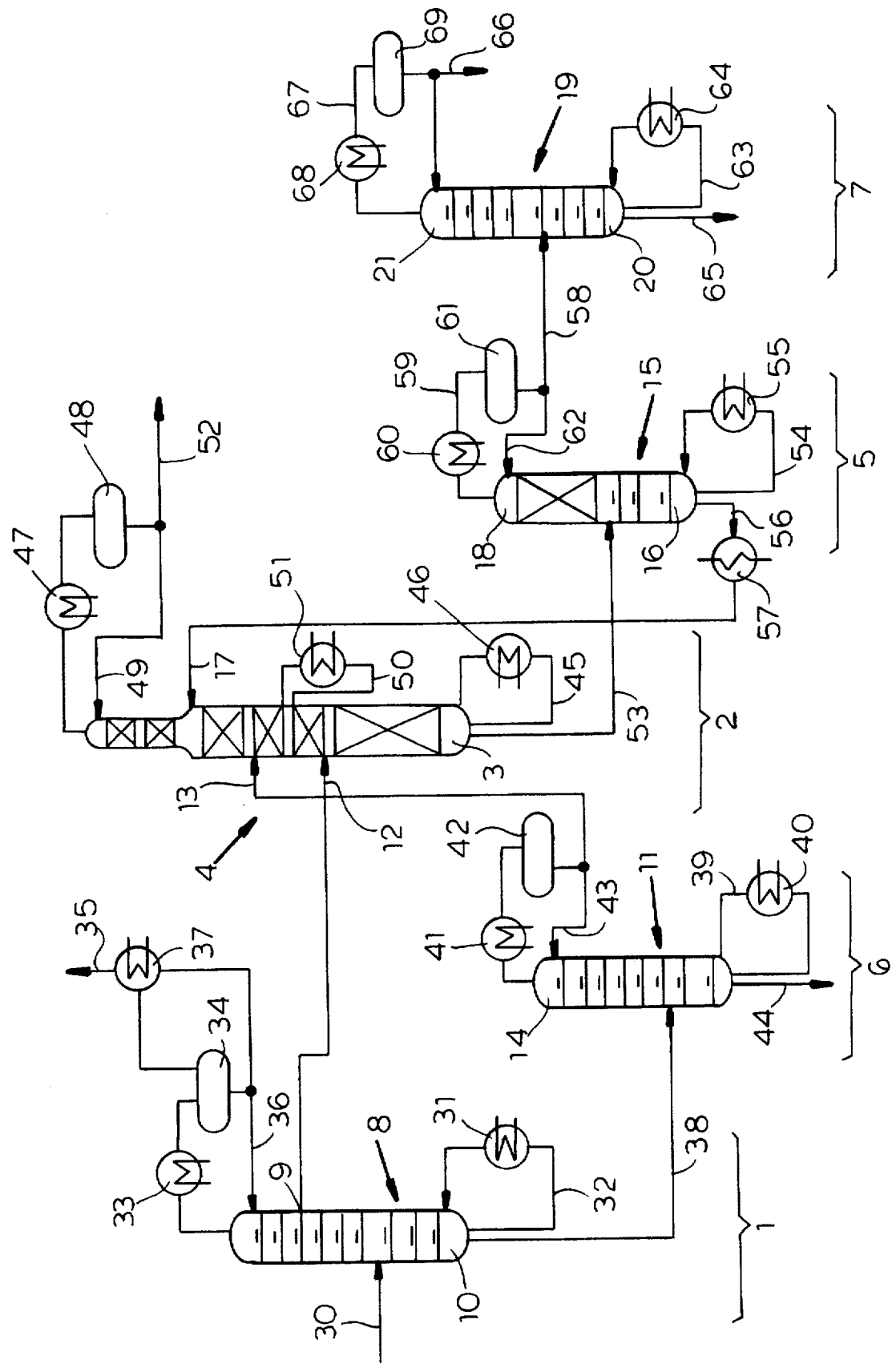

PROCESS FOR RECOVERING PURE BENZENE AND PURE TOLUENE FROM AROMATIC HYDROCARBON PRODUCTS

FIELD OF THE INVENTION

The present invention relates to a process for recovering pure benzene and pure toluene from a starting product containing aromatic hydrocarbons. More particularly this invention relates to a process for producing high purity benzene and high purity toluene.

BACKGROUND OF THE INVENTION

In a conventional recovery of the substantially pure benzene and substantially pure toluene from aromatic hydrocarbon mixtures or products containing same, the starting product can be freed from gases in a distillative stabilizing process stage. The stabilized starting product is then separated into a benzene rich and toluene rich intermediate product which can be fed to an extractive distillation process stage. The latter can include a multiplate extractive distillation column from which a mixture of the benzene and toluene and an extraction agent or solvent is withdrawn from the sump.

The extraction agent is removed from this mixture in a stripper process stage and is recycled to the extractive distillation process stage.

The products are substantially pure benzene and substantially pure toluene, i.e. benzene and toluene which are pure in the technological sense, i.e. contain only insignificant amounts of impurities.

The aromatic hydrocarbon starting product is, as a rule, a crude benzene product produced in a coking plant or pyrolysis aromatic hydrocarbon products produced in the processing of petroleum. The starting product can also be derived from the gasification of coal or petroleum (i.e. so-called gasification benzene) or a catalytic reformate formed in petroleum process.

All of these starting products or raw materials contain not only benzene, but also toluene and residual gases like hydrogen sulfide, ammonia and hydrogen.

The gas containing products are frequently referred to as unstabilized starting materials and these must be stabilized by freeing them from these residual gases so that detrimental reactions from the presence of these gases cannot occur in further processing.

The stabilization step is carried out generally in a distillative stabilizing step in which the unstabilized starting product is fed to a stabilizing column, the driven off residual gases are withdrawn from the head of the column and the stabilized product is collected in the sump of the column.

In an extractive distillation process step following the stabilization and utilizing an extractive distillation process column, the sump product of the stabilizing stage is treated with a selective solvent having polar groups and forming an extracting agent which can be supplied, as a rule, at the head of the extraction distillation column. The partial pressure of nonaromatics is increased more significantly than the partial pressure of aromatics so that nonaromatics are separated out in the extractive distillation column. In particular, the nonaromatics are withdrawn from the head of the extraction distillation column. The extraction solvent with the aromatics dissolved therein, namely, benzene and toluene, collects in the sump of the extraction distillation column.

In a stripper process stage, e.g. in a stripper distillation column, the extraction solvent is separated from the aromatics. The sump mixture of this column consists practically exclusively of benzene and toluene and thus can be considered a high purity mixture of benzene and toluene.

The distillative stabilizing stage solvent can be separated and recycled to the column. The sump product can be separated practically into the respective components, i.e. the benzene and toluene which are practically pure.

This process has been found to be successful and is described, for example, in EP 04 34 959 A2.

In this system, the stabilized product, before being subjected to the extractic stage, is separated into a benzene rich intermediate and a toluene rich intermediate in a distillation column. The benzene rich intermediate is withdrawn from the head of this distillation column and the toluene rich intermediate from a side outlet of the distillation column at an intermediate location along its height. High boiling components of the stabilized starting product collect in the sump of the distillation column and are discharged.

While this process has been successful as noted, nevertheless improvement is desirable since the purity of the benzene and toluene which results can be improved.

As to this it may be noted that the product benzene contains nonaromatic hydrocarbons of about 0.1% while the toluene contains nonaromatic hydrocarbons in an amount of about 0.2%.

DE 15 43 119 A1 describes a process for recovering benzene and toluene from an aromatic hydrocarbon product which can yield pure benzene but relatively impure toluene, the latter contained with about 1.5 weight percent of nonaromatic hydrocarbons.

This latter process operates with an initial distillation process stage in which components boiling above 150° C. are separated from the stabilized raw material.

This prepurified raw material is supplied to a single plate extractive distillation column without prior separation. In this system the extractive distillation process stage is operated discontinuously and the operation is interrupted from time to time to free the impure toluene from the detrimental nonaromatic hydrocarbons by means of extractive distillation. The product is very pure benzene and also very pure toluene. The disadvantage of this process, however, is the discontinuous operation and the need for large tanks for the intervening storage of prepurified product and impure toluene. Such tanks are expensive. In addition, the discontinuous process is energetically unsatisfactory since considerable qualities of high pressure steam are required.

Instead of the discontinuous process a second extractive distillation process stage can be provided for the after treatment of the impure toluene. This also is expensive.

OBJECTS OF THE INVENTION

It is, therefore, the principal object of the present invention to provide an improved method of producing high purity benzene and high purity toluene from aromatic hydrocarbon starting materials whereby these drawbacks are obviated.

Another object of the invention is to provide a process for recovering high purity benzene and high purity toluene from aromatic hydrocarbons containing raw materials of the type described whereby the benzene and toluene are practically completely free from nonaromatic hydrocarbons and the process is highly economical from an energy point of view.

Still another object of the invention is to provide an improved process for obtaining high purity benzene and high purity toluene with low contents of foreign substances, especially nonaromatic hydrocarbons, without a significant increase in cost.

SUMMARY OF THE INVENTION

These objects and others are attained, in accordance with the invention in a method of the type described wherein the distillative stabilizing process step for removing the gases from the starting material, is so constructed or carried out that the starting material is immediately divided into a benzene rich intermediate product and a toluene rich intermediate product and wherein the benzene rich intermediate product is fed to the extractive distillative process stage directly from the distillative stabilization process stage, while the toluene rich intermediate, before being fed to the extractive distillation stage, is depleted in high boiling components in a predistillation stage.

The process of the invention thus can comprise the steps of:

(a) degassing a starting product containing aromatic hydrocarbons including benzene and toluene in a distillative stabilizing stage and separating a resulting stabilized starting product into a benzene-rich component and a toluene-rich component;

(b) passing the toluene-rich component through a predistillation stage to deplete the toluene-rich component from high boiling point compounds;

(c) passing the benzene-rich component directly and the toluene-rich component after passing through the predistillation stage through a multi-plate extractive-distillation column in an extractive distillation stage and recovering a mixture of benzene, toluene and an extraction agent from a sump of the column;

(d) removing the extraction agent from the mixture in a stripper stage and recycling removed extraction agent to the extractive distillation stage, thereby forming a mixture of toluene and benzene of high purity; and (e) distillatively separating the mixture of toluene and benzene of high purity into substantially pure benzene and substantially pure toluene.

The invention utilizes the fact that without a special distillation stage following the stabilizing stage, the stabilizing stage can be equipped or operated so that it not only drives off detrimental residual gases, but simultaneously can divide the starting product into benzene rich and toluene rich intermediates.

A distillation stage downstream of the stabilizing stage can serve exclusively to remove the high boiling components from the toluene rich intermediate and thus this predistillation stage can be of comparatively small dimensions to process the relatively low volume of the toluene rich intermediate. The result is high purity benzene and high purity toluene in a continuous process without the need for expensive storage tanks for intervening storage of any component and without the need for additional extractive distillation process steps.

The result is end products with especially high purity and essentially the same cost as for earlier methods. The energy utilization is substantially the same as in earlier techniques as well. The invention thus provides a surprisingly synergistically effective way of improving the purity of the end products, especially with respect to the absence of nonaromatic compounds in the benzene and toluene, without any significant increase in cost.

According to the invention, the benzene rich component is withdrawn from the distillative stabilizing column at a side outlet while the toluene rich component is withdrawn from the sump. The distillative stabilizing stage of the process is operated under conditions in which the toluene rich component contains 10 to 40% benzene and preferably around 20% benzene.

The predistillation stage with which the high boiling point consequently are removed from the toluene rich component is carried out so that components with boiling points above about 120° C. are completely removed from the toluene rich component.

The extracting solvent is preferably N-substituted morpholine whose substituents have less than 8 carbon atoms or mixtures thereof. A preferred solvent is N-formyl morpholine.

According to another feature of the invention, the extractive distillation column has about 70 theoretical plates and the toluene rich component is introduced some 20 theoretical plates below the extraction agent while the benzene rich component is introduced from 40 theoretical plates below the extraction solvent. The head of the stripper column is connected to a distillation column in which the pure benzene and pure toluene are separated from one another.

The apparatus of the present invention can comprise:

means forming a distillative stabilizing stage including at least one column having a side fitting and a sump for degassing a starting product containing aromatic hydrocarbons including benzene and toluene in a distillative stabilizing stage and separating a resulting stabilized starting product into a benzene-rich component discharged from the side fitting and a toluene-rich component discharged from the sump;

means forming a predistillation stage receiving the toluene-rich component for depleting the toluene-rich component from high boiling point compounds;

means for passing the benzene-rich component directly and the toluene-rich component after passing through the predistillation stage through a multi-plate extractive-distillation column in an extractive distillation stage and recovering a mixture of benzene, toluene and an extraction agent from a sump of the extractive-distillation column;

a stripper for removing the extraction agent from the mixture in a stripper stage and recycling removed extraction agent to the extractive distillation stage, thereby forming a mixture of toluene and benzene of high purity at a head of the stripper; and a column for distillatively separating the mixture of toluene and benzene of high purity into substantially pure benzene and substantially pure toluene.

Advantageously, the column of the distillative stabilizing stage has about 60 plates and the side fitting is located at about the fifty second plate from below, the predistillation stage has a predistillation column with about 65 plates, the extractive distillation column has about 70 theoretical plates and the toluene-rich component is introduced to the extractive distillation column approximately 20 theoretical plates below introduction of the extraction agent and the benzene-rich component is introduced to the extractive distillation column approximately 40 theoretical plates below introduction of the extraction agent.

According to a feature of the invention, the column for distillatively separating the mixture of toluene and benzene is a fractionation column connected to a head of the stripper column and provided with about 60 plates, pure benzene being recovered from a head of the fractionation column, pure toluene being recovered from a sump of the fractionation column.

BRIEF DESCRIPTION OF THE DRAWING

The above and other objects, features, and advantages will become more readily apparent from the following description, reference being made to the accompanying drawing in which the sole FIGURE designated FIG. 1 is a flow diagram illustrating an apparatus for carrying out the process of the invention.

SPECIFIC DESCRIPTION AND EXAMPLE

From the drawing it will be apparent that a raw benzene product, namely, a starting materials containing benzene and toluene among its aromatic compounds is fed at 30 to a distillative stabilizing process stage 1 which is disposed upstream of and extractive distillation stage 2, a stripper stage 5 and a final distillation and separation stage 7.

The distillation stage, at which a toluene rich component has high boiling point compounds removed therefrom, is found at 6 between the stabilizing stage 1 and the extractive distillation stage 7.

The stabilization column 8 of the distillative stabilization stage 1 is a multiplate column receiving the feed 30 at an intermediate location above its sump 10. The sump product is boiled by circulation through a heating unit 31 in the sump recirculation path 32 while the head product is condensed at 33 and the liquid phase is separated at 34 before being recycled at 36 to the column 8. The vapors are discharged at 35 through a cooler 37.

Thus the stabilizing column 8, with a side outlet 9 for the benzene-rich component, serves to liberate gases from the raw material and to separate the raw material into the benzene rich component and a toluene rich component which is discharged from the sump 10 via a line 38. The column 8 can have about 60 practical plates and the side outlet 9 can be located at about the 50 second practical plate from the bottom.

The toluene-rich component is fed by the line 38 to an intermediate location of a predistillation column 11 of the predistillation stage 6. The column 11 is provided with a recirculation path 39 and a heater 40 for heating the sump product, the vapors travelling upwardly through the column 11. A cooler 41 condenses these vapors 1 at 42 are partly returned at 43 as a condensate to the head 14 of the column. The head 14 of the column 11 is connected via line 13 with the extractive distillation column 4 of the extractive distillation stage 2. The sump product, namely, the higher boiling components originally present in the toluene ring component, are discharged at 44.

The predistillation column 11 has about 65 practical plates.

The extraction distillation column 4 has an inlet 12 supplying the benzene rich component to the extractive distillation column and an inlet 13 supplying the toluene rich component thereto. The sump product is boiled by circulation at 45 through a heater 46, while the heated product is condensed by passage of the vapors through a cooler 47 and a collector 48 before return of the condensate at 49.

An inlet 17 is provided at an upper portion of the extraction distillation column 4, below the distillation portion, to supply recycled extraction solvent to this column. The extraction distillation column 4 can contain about 70 theoretical plates and the inlet 13 is preferably provided at some 20 theoretical plates below the solvent inlet 17 while the inlet 12 for the benzene ring component is provided some 40 theoretical plates below the extraction solvent 15. Between the inlets 12 and 13, a chimney plate can be provided as one of the plates of the system.

A loop 50 with a heater 51 can be provided in conjunction with a chimney plate or the like upon which a liquid can collect until it overflows, to draw off a portion of that liquid and heat it to boiling in the heater 51.

Gases which are discharged from the system at 52 are of lower molecular weight hydrocarbons.

The sump product, consisting of a mixture of benzene, toluene and the extraction solvent, is fed via line 53 to an intermediate portion of the stripper 15 of the stripper stage 5. The stripper column 15 has a boiler for the sump 16 consisting of the loop 54 and the heater 55. The sump product withdrawn at 56 is substantially exclusively the solvent which upon cooling at 57, is returned to the inlet 17. The vapors, consisting of a mixture of toluene and benzene, is withdrawn from the head 18 of the stripper 15 at line 58 and supplied to a distillation column 19. The head 18 of the stripper column is provided with a cooling loop 59 with a cooler 60, a collection vessel 61 and a condensate return at 62. The fractionation column 19, connected to the head 18 of the stripper column 15, has a boiler loop 63 with a heater 64 connected to the sump 20 and discharges practically pure toluene from the outlet 65. A heat product is discharged at 66 from the cooling loop 67 with its cooler 68 and collection tank 69 in the form of practically pure benzene. The head 21 of this column is separated from the sump 20 by substantially 60 practical plates.

The various heating and cooling units from the boilers and refluxers for the column are, of course, conventional for such columns.

With the apparatus of the invention, the starting product is freed from gases in the stabilization stage 1 which simultaneously stabilizes the starting product and the benzene rich and toluene rich components. The benzene rich component is withdrawn from the side outlet 9 of the stabilizing column 8 and fed directly to the extraction distillation column. The toluene rich component is withdrawn from the sump 10 of the stabilizing column and is subjected to predistillation in the column 11. This product contains about 20 (±5) % benzene. Methylcyclohexane in the starting product can make up up to about 70% of the toluene rich component.

While the benzene rich component is fed directly to the distillative stabilizing stage, the toluene rich component is subjected to the predistillation in which the high boiling components, i.e. components with a boiling point of 120° C. or more are removed. These components are usually aromatic hydrocarbons with more than 7 carbon atoms and higher nonaromatic hydrocarbons.

In the extractive distillation stage 2 N-morpholine is used as the extracting solvent (see DE 15 68 940 C3). The extracting solvent is supplied at the head of the extraction distillation column 4 and a mixture of the pure benzene, pure toluene and extraction solvent are withdrawn from the sump 3.

In the stripper stage 5, the extraction solvent is separated from the mixture of benzene and toluene and is recycled to the extractive distillation stage. The mixture from the stripping stage consisting essentially only of benzene and toluene is then separated by distillation at 7 with high selectivity. A comparative test between the invention and the process of EP 04 34 959 A2 is found in the following Table.

TABLE I

|  | PROCESS ACCORDING TO THE INVENTION | PROCESS ACCORDING TO EP 04 34 959 A2 |
| --- | --- | --- |
| BENZENE YIELD | 98.90% | 98.48 |
| TOLUENE YIELD | 94.85 | 98.33 |
| NONAROMATIC IN BENZENE < | 0.012% | 0.093% |
| NONAROMATIC IN TOLUENE < | 0.051% | 0.202% |

It will be apparent that, with the invention, not only is the purity of the benzene significantly improved but also that an increase in the yield can surprisingly be obtained. This is especially important because benzene losses pose a danger to the environment and benzene can only be removed from gases discharged into the atmosphere. The cost of treating gases and the like released into the atmosphere is thus removed with the system of the invention. With toluene it is also an increased purity but at the cost of a slight decrease in yield. Otherwise, the energy and apparatus cost are similar to the prior art. By comparison with DE 15 43 119, purity and yield are similar but the apparatus costs are substantially less since large tanks for intervening holding of materials are not required.

Furthermore, the invention can operate with ⅓ less superheated steam.

We claim:

1. A process for recovering benzene toluene free of non-aromatic hydrocarbons from a starting product and containing aromatic hydrocarbons, said process comprising the steps of:
   (a) degassing a starting product containing aromatic hydrocarbons including benzene and toluene in a distillative stabilizing stage to drive off residual gases and separating a resulting stabilized starting product into a benzene-rich component and a toluene-rich component Wherein said benzene-rich component is withdrawn from a distillative stabilizing column of said distillative stabilizing stage at a side fitting at an intermediate height of said distillative stabilizing column and said toluene-rich component is withdrawn from said distillative stabilizing column of said distillative stabilizing stage at a sump thereof;
   (b) passing said toluene-rich component through a predistillation stage to deplete said toluene-rich component from high boiling point compounds;
   (c) passing said benzene-rich component directly and said toluene-rich component after passing through said predistillation stage through a multi-plate extractive-distillation column in an extractive distillation stage and recovering a mixture of benzene, toluene and an extraction agent from a sump of said column;
   (d) removing said extraction agent from said mixture in a stripper stage and recycling removed extraction agent to said extractive distillation stage, thereby forming a purified mixture of toluene and benzene; and
   (e) distillatively separating the purified mixture of toluene and benzene into purified benzene and purified toluene.

2. The process defined in claim 1 wherein said toluene-rich component contains 10 to 40% benzene.

3. The process defined in claim 2 wherein said toluene-rich component contains about 20% benzene.

4. The process defined in claim 2 wherein, in step (b), compounds having a boiling point above about 120° C. are removed from said toluene-rich component.

5. The process defined in claim 4 wherein said extraction agent is an N-substituted morpholine whose substituents have less than eight carbon atoms or mixtures thereof.

6. The process defined in claim 5 wherein said extraction agent is N-formylmorpholine.

7. The process defined in claim 5 wherein said extractive distillation column has about 70 theoretical plates, said toluene-rich component is introduced to said extractive distillation column approximately 20 theoretical plates below introduction of said extraction agent and said benzene-rich component is introduced to said extractive distillation column approximately 40 theoretical plates below introduction of said extraction agent.

8. The process defined in claim 1 wherein said toluene-rich component contains 10 to 40% benzene.

9. The process defined in claim 8 wherein said toluene-rich component contains about 20% benzene.

10. The process defined in claim 1 wherein, in step (b), compounds having a boiling point above about 120° C. are removed from said toluene-rich component.

11. The process defined in claim 1 wherein said extraction agent is an N-substituted morpholine whose substituents have less than eight carbon atoms or mixtures thereof.

12. The process defined in claim 11 wherein said extraction agent is N-formylmorpholine.

13. The process defined in claim 1 wherein said extractive distillation column has about 70 theoretical plates, said toluene-rich component is introduced to said extractive distillation column approximately 20 theoretical plates below introduction of said extraction agent and said benzene-rich component is introduced to said extractive distillation column approximately 40 theoretical plates below introduction of said extraction agent.

14. An apparatus for recovering benzene and toluene free of non-aromatic hydrocarbons from a starting product containing aromatic hydrocarbons, said apparatus comprising:

means forming a distillative stabilizing stage including at least one column having a side fitting and a sump for degassing a starting product containing aromatic hydrocarbons including benzene and toluene in a distillative stabilizing stage and separating a resulting stabilized starting product into a benzene-rich component discharged from said side fitting and a toluene-rich component discharged from said sump;

means forming a predistillation stage receiving said toluene-rich component for depleting said toluene-rich component from high boiling point compounds;

means for passing said benzene-rich component directly and said toluene-rich component after passing through said predistillation stage through a multi-plate extractive-distillation column in an extractive distillation stage and recovering a mixture of benzene, toluene and an extraction agent from a sump of said extractive-distillation column;

a stripper for removing said extraction agent from said mixture in a stripper stage and recycling removed extraction agent to said extractive distillation stage, thereby forming a purified mixture of toluene and benzene at a head of said stripper; and a column for distillatively separating the purified mixture of toluene and benzene into purified benzene and purified toluene.

15. The apparatus defined in claim 14 wherein said column of said distillative stabilizing stage has about 60 plates and said side fitting is located at about the fifty second plate from below, said predistillation stage has a predistillation column with about 65 plates, said extractive distillation column has about 70 theoretical plates and said toluene-rich component is introduced to said extractive distillation column approximately 20 theoretical plates below introduction of said extraction agent and said benzene-rich component is introduced to said extractive distillation column approximately 40 theoretical plates below introduction of said extraction agent.

16. The apparatus defined in claim 15 wherein said column for distillatively separating the mixture of toluene and benzene is a fractionation column connected to a head of said stripper column and provided with about 60 plates, pure benzene being recovered from a head of said fractionation column, pure toluene being recovered from a sump of the fractionation column.

* * * * *